United States Patent
Razansky et al.

(10) Patent No.: US 10,743,839 B2
(45) Date of Patent: Aug. 18, 2020

(54) DEVICE AND METHOD FOR HYBRID OPTOACOUSTIC TOMOGRAPHY AND ULTRASONOGRAPHY

(71) Applicant: Helmholtz Zentrum Muenchen Deutsches Forschungszentrum fuer Gesundheit und Umwelt (GmbH), Neuherberg (DE)

(72) Inventors: Daniel Razansky, Munich (DE); Xose Luis Dean-Ben, Munich (DE)

(73) Assignee: Helmholtz Zentrum Muenchen Deutsches Forschungszentrum fuer Gesundheit und Umwelt (GmbH), Neuherberg (DE)

( * ) Notice: Subject to any disclaimer, the term of this patent is extended or adjusted under 35 U.S.C. 154(b) by 1033 days.

(21) Appl. No.: 15/174,572

(22) Filed: Jun. 6, 2016

(65) Prior Publication Data
US 2016/0361042 A1    Dec. 15, 2016

(30) Foreign Application Priority Data
Jun. 10, 2015    (EP) ..................... 15171426

(51) Int. Cl.
*A61B 8/00*    (2006.01)
*A61B 5/00*    (2006.01)
(Continued)

(52) U.S. Cl.
CPC .......... *A61B 8/4416* (2013.01); *A61B 5/0095* (2013.01); *A61B 8/0825* (2013.01);
(Continued)

(58) Field of Classification Search
CPC ... A61B 8/4416; A61B 8/5261; A61B 8/4455; A61B 5/0095; A61B 8/4483; G01S 15/8965
See application file for complete search history.

(56) References Cited

U.S. PATENT DOCUMENTS

| | | | | |
|---|---|---|---|---|
| 4,694,700 A | * | 9/1987 | Maerfeld | G01S 7/52063 73/625 |
| 5,103,129 A | * | 4/1992 | Slayton | B06B 1/0622 310/334 |

(Continued)

OTHER PUBLICATIONS

"Biomedical Applications of Photoacoustic Imaging with Exogenous Contrast Agents" by G.P. Luke et al. Annals of Biomedical Engineering, vol. 40, No. 2, Feb. 2012 pp. 422-437.*

(Continued)

*Primary Examiner* — Jeffrey G Hoekstra
*Assistant Examiner* — Jason M Ip
(74) *Attorney, Agent, or Firm* — Sheridan Ross P.C.

(57) ABSTRACT

The invention includes a device and a method for hybrid optoacoustic and ultrasonographic imaging of an object. The device comprises: an irradiation unit configured to irradiate the object with electromagnetic radiation; first transducer elements configured to detect ultrasound waves generated in the object upon irradiating the object with the electromagnetic radiation; second transducer elements configured to detect ultrasound waves reflected and/or transmitted by the object; a surface comprising at least one first surface segment, on which the first transducer elements are arranged, and at least one second surface segment, on which the second transducer elements are arranged. The first surface segment and/or the second surface segment have a curved shape. The first transducer elements have a first size and pitch and second transducer elements have a second size and pitch, wherein the first pitch and second pitch are different and/or the first size and second size are different.

13 Claims, 6 Drawing Sheets

(51) Int. Cl.
*A61B 8/14* (2006.01)
*G01S 15/89* (2006.01)
*A61B 8/08* (2006.01)

(52) U.S. Cl.
CPC .............. *A61B 8/14* (2013.01); *A61B 8/4455* (2013.01); *A61B 8/4494* (2013.01); *A61B 8/5207* (2013.01); *A61B 8/5261* (2013.01); *G01S 15/8915* (2013.01); *G01S 15/8965* (2013.01); *A61B 8/4483* (2013.01)

(56) References Cited

U.S. PATENT DOCUMENTS

| | | | |
|---|---|---|---|
| 2011/0088477 A1 | 4/2011 | Someda et al. | |
| 2011/0208057 A1* | 8/2011 | Oikawa | A61B 5/0095 600/443 |
| 2014/0163353 A1 | 6/2014 | Razansky et al. | |
| 2015/0119682 A1* | 4/2015 | Nagae | A61B 5/004 600/407 |

OTHER PUBLICATIONS

European Search Report prepared on Oct. 16, 2015 by the European Patent Office for European Application No. EP 15 17 1426.

* cited by examiner

DEVICE AND METHOD FOR HYBRID OPTOACOUSTIC TOMOGRAPHY AND ULTRASONOGRAPHY

CROSS-REFERENCE TO RELATED APPLICATIONS

This application claims the benefit of European Patent Application No. EP 15 17 1426 filed Jun. 10, 2015, the entire contents of which are incorporated herein by reference.

DESCRIPTION

The present invention relates to a device and a method for hybrid optoacoustic and ultrasonographic imaging of an object according to the independent claims.

Ultrasonography is an ultrasound-based diagnostic imaging technique used for visualizing internal body structures. Compared to other prominent methods of medical imaging, ultrasonography has several advantages. It provides images in real-time (rather than after an acquisition or processing delay), it is portable and can be brought to a sick patient's bedside, it is substantially lower in cost, and it does not use harmful ionizing radiation.

Optoacoustic imaging is based on the physical effect, also referred to as optoacoustic effect, according to which ultrasonic waves are generated due to absorption of electromagnetic radiation by an object, for example a biological tissue, and a subsequent thermoelastic expansion of the object. Thus, optoacoustic imaging is a non-invasive hybrid technique making use of optical absorption and ultrasonic wave propagation and allowing for structural, functional and molecular imaging. Thereby it has the high contrast of optical imaging and the ability to obtain images from deep tissues with high (ultrasonic) resolution independent of light scattering.

Hybrid optoacoustic and ultrasonographic imaging is aimed at combining the advantages and complementary contrasts of both methods.

The invention is based on the problem of providing a device and a corresponding method for improved hybrid optoacoustic and ultrasonographic imaging of an object, in particular in order to obtain both optoacoustic and ultrasonographic images having high image quality and allowing for quantitative conclusions.

The problem is solved by the device and the method according to the independent claims. Preferred embodiments of the invention are part of the dependent claims.

According to an aspect of the invention, a device for hybrid optoacoustic and ultrasonographic imaging of an object comprises an irradiation unit configured to irradiate the imaged object with electromagnetic radiation, first transducer elements configured to detect ultrasound waves generated in the imaged object upon irradiating the object with the electromagnetic radiation, second transducer elements configured to detect ultrasound waves reflected and/or transmitted by the object, and a surface comprising at least one first surface segment, on which the first transducer elements are arranged, and at least one second surface segment, on which the second transducer elements are arranged. The at least one first surface segment and/or the at least one second surface segment having a curved shape and said first transducer elements having a first size and a first pitch and said second transducer elements having a second size and a second pitch, wherein the first pitch is different from the second pitch and/or the first size is different from the second size.

According to another aspect of the invention, a method for hybrid optoacoustic and ultrasonographic imaging of an object comprises the following steps: irradiating the imaged object with electromagnetic radiation; detecting ultrasound waves generated in the object upon irradiating the object with the electromagnetic radiation by a plurality of first transducer elements, which are arranged on at least one first surface segment of a surface; and detecting ultrasound waves, which are reflected and/or transmitted by the object, by second transducer elements, which are arranged on at least one second surface segment of the surface.

The at least one first surface segment and/or the at least one second surface segment having a curved shape, said first transducer elements having a first size and a first pitch and said second transducer elements having a second size and a second pitch, wherein the first pitch is different from the second pitch and/or the first size is different form the second size.

According to yet another aspect of the invention, a method for hybrid optoacoustic and ultrasonographic imaging of an object comprises the following steps: irradiating the imaged object with electromagnetic radiation; detecting first ultrasound waves generated in the object upon irradiating the object with the electromagnetic radiation by a plurality of first transducer elements, which are arranged on at least one first surface segment of a surface; and detecting second ultrasound waves, which are reflected and/or transmitted by the object, by a plurality of second transducer elements, which are arranged on at least one second surface segment of the surface. Preferably, said second ultrasound waves are emitted in response to absorption of electromagnetic radiation in absorbing structures located outside the imaged object, such as the surface of the transducer or additional absorbing structures placed between the imaged object and the transducer. Preferably, the at least one first surface segment and/or the at least one second surface segment having a curved shape, said first transducer elements having a first size and a first pitch and said second transducer elements having a second size and a second pitch, wherein the first pitch is different from the second pitch and/or the first size is different form the second size.

In the sense of the present invention, the term "pitch" in connection with transducer elements preferably relates to the distance between the centers of neighboring transducer elements, i.e. transducer elements which are bordering each other.

An aspect of the invention is based on the approach to detect optoacoustic signals, i.e. ultrasound waves generated in the object in response to an irradiation of the object with electromagnetic radiation, by first transducer elements and to generate and detect ultrasonographic signals, i.e. ultrasound waves reflected and/or transmitted by the object in response to an irradiation of the object with ultrasound waves, by second transducer elements, wherein the geometrical properties and/or the geometrical arrangement of the first and second transducer elements are different. In particular, the first and second transducer elements have a different element pitch and/or different size, i.e. the size of the first detector elements is different from the size of the second detector elements and/or the pitch of the first detector elements is different from the pitch of the second transducer elements. Alternatively or additionally, the first and/or second transducer elements are provided on a curved surface segment of a detector surface. As a result, ultrasound waves emerging from the object are detected by an arrangement of transducer elements on a detector surface, wherein the properties and/or arrangement of the first transducer elements provided on a first segment of the detector surface can be optimized for optoacoustic signal detection, while the properties and/or arrangement of the second transducer elements provided on a second segment, which is different from the first segment, of the detector surface can be optimized for ultrasonographic signal generation and detection.

Yet another aspect of the invention is based on the concept to provide specifically designed hybrid transducer array configurations having a spatial distribution of the transducer elements that allow for improved real-time imaging performance in both the optoacoustic and ultrasound imaging mode. The transducer array configurations are suitable for both stationary and handheld imaging devices for two- and three-dimensional imaging. Preferably, a non-uniform distribution of the first and second transducer elements is provided, wherein the spatial distribution and/or size of the first transducer elements forming a part of the transducer array is optimized for optoacoustic imaging, while the spatial distribution and/or size of the second transducer elements forming the remaining part of the transducer array is optimized for ultrasonographic imaging. For example, the part of the array that is optimally configured for ultrasonographic imaging, i.e. for ultrasound emission and detection, may have different geometries depending on the particular application and/or the type of the imaged object, for example convex or linear when two-dimensional imaging is performed, or planar or spherical for three-dimensional imaging. The other part of the array that is configured for optoacoustic imaging, i.e. for detecting ultrasound waves generated in the object upon irradiation with electromagnetic radiation, may have geometries that are independent from the geometry of the ultrasonographic imaging part of the array, for example a concave, linear, planar, spherical or cylindrical shape. In general, irregular shapes of the transducer array may also be provided to provide optimal tomographic coverage depending on the exact shape of the imaged object. In general, size and pitch of the first transducer elements are different from size and pitch of the second transducer elements provided in the different parts of the array. Further, the image formation procedure may also be different for the two modalities, e.g. the ultrasonographic part is operated in a pulse-echo mode providing images based on line-by-line beamforming, whereas optoacoustic signals can be simultaneously captured to form images using a tomographic reconstruction algorithm, such as two- or three-dimensional Radon transform, back-projection or model-based inversion algorithm. Preferably, signals detected by the ultrasound part of the array may be additionally used for optoacoustic image formation and vice versa. In addition or alternatively, the part of the array optimized for optoacoustic imaging can be also configured to emit ultrasound, thus additionally used in order to form reflection- or transmission-based ultrasound images.

In summary, aspects of the invention allow for improved hybrid optoacoustic and ultrasonographic imaging of an object, in particular for obtaining both optoacoustic and ultrasonographic images having high image quality and allowing for quantitative conclusions.

According to another preferred embodiment, the first surface segment and/or the second surface segment is or are configured to generate ultrasound waves in response to absorption of electromagnetic radiation. Thereby, ultrasound waves are generated by the first and/or second surface segment due to the optoacoustic effect, emitted towards the imaged object and, after reflection and/or transmission by the imaged object, detected by the second transducer elements.

According to another preferred embodiment, an absorbing element is provided between the imaged object and the first surface segment and/or the second surface segment, the absorbing element being configured to generate ultrasound waves in response to an absorption of electromagnetic radiation. Similarly to the embodiment set forth above, ultrasound waves are generated by the absorbing element due to the optoacoustic effect, emitted towards the imaged object and, after reflection and/or transmission by the imaged object, detected by the second transducer elements.

Preferably, the absorbing element being configured to generate high-frequency ultrasound waves in response to an absorption of short-pulsed electromagnetic radiation. Alternatively or additionally, the absorbing element comprising at least one electromagnetic radiation absorbing microsphere having a diameter in the range between 50 µm and 500 µm, preferably approximately 100 µm, and/or emitting ultrasound waves exhibiting a peak frequency in the range between 4 MHz and 10 MHz, preferably approximately 7.5 MHz, in response to an absorption of a laser pulse having a duration below 100 ns, preferably below approximately 10 ns. Alternatively or additionally, the absorbing element comprising at least one electromagnetic radiation absorbing foil configured to emit broadband planar ultrasound waves in response to an absorption of short laser pulses.

Preferably, the second transducer elements are configured to both emit ultrasound waves towards the object and to detect ultrasound waves reflected and/or transmitted by the object.

According to a preferred embodiment, at least one first surface segment has a concave shape. Thereby, the first transducer elements, which detect the optoacoustic signals, are arranged along at least one concave first surface segment.

According to another preferred embodiment, at least one second surface segment has a convex shape or a planar shape. Accordingly, the second transducer elements, which emit and detect ultrasound waves, are arranged along at least one convex and/or at least one planar second surface segment.

According to yet another preferred embodiment, the first pitch is larger than the second pitch. Preferably, the center-center distance between two neighboring first transducer elements is larger than the center-center distance between two neighboring second transducer elements.

Preferably, the first pitch is at least 1.5 times and/or at least twice and/or at least 2.5 times and/or at least three times the second pitch.

It is, moreover, preferred that the first size of the first transducer elements is larger than the second size of the second transducer elements.

Preferably, the first size is at least 1.5 times and/or at least twice and/or at least 2.5 times and/or at least three times the second size.

Each of the preferred embodiments set forth above, taken alone or in combination, further improves quality and quantitative and/or diagnostic conclusiveness of both optoacoustic and ultrasonographic images obtained.

According to a further preferred embodiment, the first transducer elements are adjacent to each other and/or the second transducer elements are adjacent to each other. Preferably, neighboring transducer elements are spatially arranged such that they adjoin each other. Preferably, the surface being a continuous surface which is formed by the at least one first surface segment and the at least one second surface segment. Additionally or alternatively, the first transducer elements provided on the first surface segment and/or the second transducer elements provided on the second surface segment form a continuous surface. One or more of the aforementioned aspects contribute to further improve image quality and quantitative and/or diagnostic conclusiveness.

According to yet another preferred embodiment, the device comprises a control unit configured to reconstruct a first image (optoacoustic image) based on the detected ultrasound waves generated in the object upon irradiating the object with the electromagnetic radiation, the first image exhibiting a first resolution and a first field of view, and to reconstruct a second image (ultrasonographic image) based on the detected ultrasound waves reflected and/or transmitted by the object.

According to another preferred aspect of the invention, the first transducer elements are configured to detect both ultrasound waves generated in the object upon irradiating the object with the electromagnetic radiation and ultrasound waves, which are reflected and/or transmitted by the object. Alternatively or additionally, the second transducer elements are configured to detect both ultrasound waves reflected and/or transmitted by the object and ultrasound waves generated in the object upon irradiating the object with the electromagnetic radiation.

Preferably, the control unit is configured to reconstruct a first image (optoacoustic image) based on ultrasound waves, which are generated in the object upon irradiating the object with the electromagnetic radiation and detected by both the first transducer elements and the second transducer elements. In this way, optoacoustic images are formed based on information received from both the first transducer elements arranged on the first surface segment(s) and the second transducer elements arranged on the second surface segment(s).

Alternatively or additionally, the control unit is configured to reconstruct a second image (ultrasonographic image) based on ultrasound waves, which are reflected and/or transmitted by the object and detected by both the first transducer elements and the second transducer elements. Accordingly, formation of ultrasound images by emitting and detecting reflected and/or transmitted ultrasound waves by both the first transducer elements arranged on the first surface segment(s) and the second transducer elements arranged on the second surface segment(s) can be performed as well.

According to a preferred embodiment, the control unit being configured to reconstruct the first image using second information, which is contained in at least one reconstructed second image, and/or to reconstruct the second image using first information, which is contained in at least one reconstructed first image. Preferably, the second information relates to locations of acoustic scatterers and/or heterogeneities in the object and is contained in at least one second image, which has been reconstructed based on the detected ultrasound waves reflected by the object, and/or the second information relates to the speed of sound and/or acoustic attenuation in the object and is contained in at least one second image, which has been reconstructed based on the detected ultrasound waves transmitted by the object. In this way, images rendered by the ultrasound part of the array may be additionally used for aiding optoacoustic image formation and vice versa. For example, the information on the location of acoustic scatterers or heterogeneities rendered by the reflection mode ultrasound images can be used as an a-priori information during reconstruction of the optoacoustic images, thus improve their quality and accuracy. Similarly, ultrasound images made in the transmission mode, which render maps of the speed of sound and acoustic attenuation in the imaged medium, can be again fed into the optoacoustic reconstruction process in order to improve spatial resolution and overall quality of the images.

Preferably, the second image exhibiting a second resolution and a second field of view, wherein at least one of the first resolution, the first field of view, the second resolution and the second field of view is or are optimized. Additionally or alternatively, the device is configured such that the resolution of the first image and the second image is matched and/or the field of view of the first image and the second image is matched. The term "matched" preferably implies that the resolution and/or the field of view of both the first image and the secand image are essentially the same or differ by a given percentage value, e.g. 2%, 5% or 10%.

Alternatively, the device is configured such that the resolution of the first image and the second image are different and/or the field of view of the first image and the second image are different. For example, the first field of view of the first image (optoacoustic image) is smaller, in particular much smaller, than the second field of view of the second image (ultrasonographic image). Preferably, the first field of view is at least two times and/or three times and/or four times smaller than the second field of view. For instance, the field of view of the ultrasonographic image may cover an entire imaged object while the field of view of optoacoustic images only covers a small portion of the imaged object. This kind of different field of view implementation is preferably used, e.g., for coarse anatomical navigation using the ultrasound modality while visualizing functional or molecular information in smaller regions using the optoacoustic modality.

Preferably, the first transducer elements have a first central frequency and the second transducer elements have a second central frequency, wherein the first central frequency is different from the second central frequency. Preferably, the first central frequency is smaller, preferably at least 1.5 times and/or 2.5 times and/or 3.5 times smaller, than the second central frequency.

According to yet another preferred embodiment, the temporal resolution of the first (optoacoustic) and second (ultrasonographic) images differ substantially. Preferably, the temporal resolution of the optoacoustic images is substantially higher than the temporal resolution of the ultrasonographic images or vice versa. For example, a fast signal dynamics can be provided only for the optoacoustic images, while ultrasonographic images are only acquired, e.g., for every 10, 20, 40, 60, 80 or 100 optoacoustic images. In other words, the temporal resolution of the ultrasonographic images is 10, 20, 40, 60, 80 or 100 times smaller than the temporal resolution of the optoacoustic images. In this way, the acquired and processed data volumes can be reduced appropriately.

Preferably, the first transducer elements have a first bandwidth and angular coverage on the basis of which the first resolution of the first image is adjustable or adjusted. Alternatively or additionally, the first field of view of the first image is adjustable or adjusted on the basis of the first size of the first transducer elements and their distance to the sample.

Preferably, the second resolution of the second image comprises a second axial resolution and a second lateral resolution and/or the second field of view comprises a second axial field of view and a second lateral field of view, wherein the control unit and the detection bandwidth of the first transducer elements are configured so that the second transducer elements emit ultrasound waves having a spatial pulse length on the basis of which the second axial resolution is adjustable or adjusted and/or the second transducer elements are configured to focus the emitted ultrasound waves to at least one focal point having a focal distance from the transducer elements, wherein the second lateral resolution is adjustable or adjusted on the basis of the focal distance and/or the second lateral resolution is adjustable or adjusted on the basis of the second size of the second transducer elements and/or the control unit is configured to perform adaptive beamforming to adjust the lateral resolution and/or the control unit is configured to control the second transducer elements to emit pulses of ultrasound waves at a pulse repetition rate, wherein the second axial field of view is adjustable or adjusted on the basis of the pulse repetition rate and/or the second lateral field of view is adjustable or adjusted on the basis of a second number of second transducer elements emitting ultrasound waves towards the object.

BRIEF DESCRIPTION OF THE DRAWINGS

The above and other elements, features, characteristics and advantages of the present invention will become more apparent from the following detailed description of preferred embodiments with reference to the figures showing.

DETAILED DESCRIPTION

Figure 1:
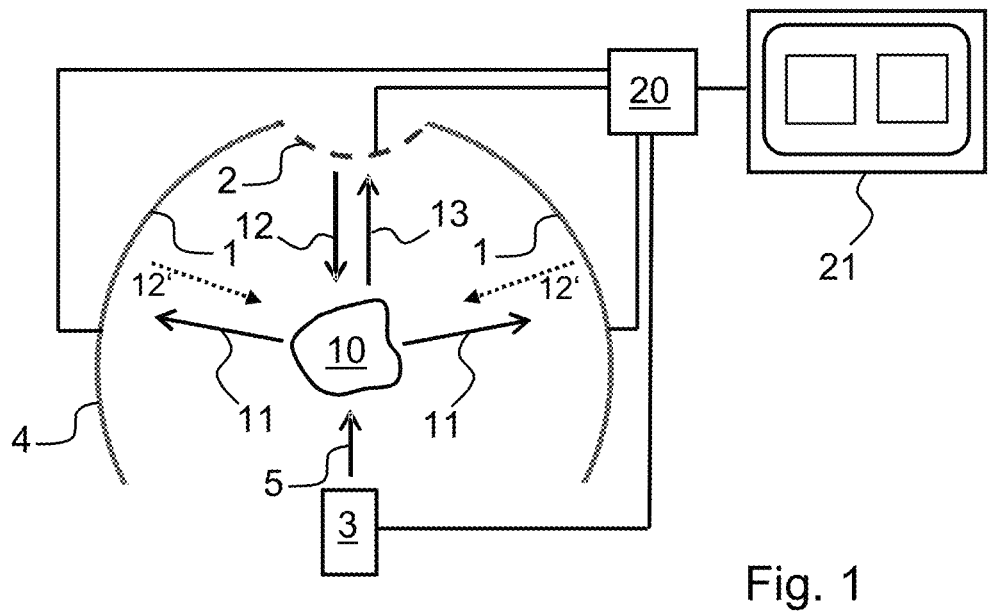
FIG. 1 a schematic representation of a first example of a device for hybrid optoacoustic and ultrasonographic imaging including a cross-sectional view of a detector unit.

FIG. 1 shows a first example of a device for hybrid optoacoustic and ultrasonographic imaging of an imaged object 10. The device comprises an irradiation unit 3 which is configured to irradiate the object 10 with electromagnetic radiation 5, for example in the visible, nearinfrared, microwave or radio frequency (RF) range. Preferably, the irradiation unit 3 is configured to emit pulsed, amplitude modulated and/or frequency modulated electromagnetic radiation towards the object 10. Due to irradiating the imaged object 10 with transient electromagnetic radiation, which is partially absorbed by the object 10, mechanical waves 11, in particular ultrasound waves, are generated and emitted by the object 10.

The device further comprises a detector unit 4 having a sensitive detector surface that is sensitive to mechanical, in particular ultrasound, waves and partially surrounds the object 10. In the present example, the detector surface comprises two first surface segments 1 having, as seen from the object 10, a concave shape and a second surface segment 2 having, as seen from the object 10, a convex shape.

The first surface segments 1 of the detector unit 4 comprise a plurality of first transducer elements which are configured to detect the ultrasound waves 11 that are generated in the object 10 upon irradiation with the electromagnetic radiation 5. The second surface segment 2 of the detector unit 4 comprises a plurality of second transducer elements which are configured and/or controlled both to emit ultrasound waves 12 towards the object 10 and to detect ultrasound waves 13, which are reflected and/or transmitted by the object 10. As a result, the detector unit 4 is configured to detect both optoacoustically generated ultrasound waves 11, which can be further processed in order to obtain optoacoustic images of the object 10, and ultrasonic waves 13, which are further processed in order to obtain ultrasonographic images of the object 10.

Alternatively or additionally, the first transducer elements of the first surface segments 1 of the detector unit 4 are configured and/or controlled both to emit ultrasound waves 12 towards the object 10 and to detect the ultrasound waves 11 that are generated in the object 10 upon irradiation with the electromagnetic radiation 5 and/or to detect ultrasound waves 13 which are reflected and/or transmitted by the object 10. Alternatively or additionally, the second transducer elements of the second surface segment 2 of the detector unit 4 are configured and/or controlled both to emit ultrasound waves 12 towards the object 10 and to detect the ultrasound waves 11 that are generated in the object 10 upon irradiation with the electromagnetic radiation 5 and/or to detect ultrasound waves 13 which are reflected and/or transmitted by the object 10. In this way, all the first and second transducer elements located on first surface segments 1 and second surface segment 2 (or any combination or sub-set of those elements) can be used to obtain both optoacoustic and ultrasonographic images of the object 10.

Preferably, the second transducer elements are piezoelectric elements which are configured to generate ultrasound waves 12 by converting electrical energy into mechanical energy in the form of ultrasound waves due to the piezoelectric effect, and vice versa. Alternatively or additionally, ultrasound waves 12' (dashed arrows) are generated by the optoacoustic effect due to absorption of electromagnetic radiation 5 outside the imaged object 10, e.g. at the first surface segment 1 and/or the second surface segment 2 of the detector unit 4. In this case, the second transducer elements are only or also, respectively, configured and/or controlled to detect ultrasound waves 13 which are, after generation due to absorption of electromagnetic radiation 5 outside the imaged object 10 and emission towards the object 10, reflected and/or transmitted by the object 10.

Preferably, the device further comprises a control unit 20 which is configured to reconstruct two-dimensional or three-dimensional optoacoustic and ultrasonographic images based on the transducer signals generated by the first transducer elements provided on the first surface segments 1 and the second transducer elements 2 provided on the second surface segment 2, respectively.

Moreover, the control unit 20 is preferably configured to control the irradiation unit 3 to irradiate the object 10 in the required manner, for example by pulsed or modulated electromagnetic radiation. Similarly, the control unit 20 is preferably configured to control the second transducer elements provided on the second surface segment 2 to emit ultrasound pulses 12 towards the object 10.

Preferably, the device may further comprise a display unit 21 which is configured to display the reconstructed two- or three-dimensional optoacoustic and ultrasonographic images. The optoacoustic and ultrasonographic images obtained from the same region of interest may be displayed in separate images or, after appropriate image fusion, in a single fused image.

The first transducer elements of the first surface segments 1 have a first size and a first pitch, which relates to the distance between the centers of neighboring or adjacent first transducer elements. The second transducer elements provided on the second surface segment 2 have a second size and a second pitch, which relates to the distance between the centers of neighboring or adjacent second transducer elements.

Preferably, the first size of the first transducer elements is different from the second size of the second transducer elements and/or the first pitch of the first transducer elements is different from the second pitch of the second transducer elements. Additionally or alternatively, the type of transducer elements used for the first transducer elements may be different from the type of transducer elements used for the second transducer elements. By means of one or more of the aforementioned measures, each of the first and second segments 1 and 2, respectively, of the detector unit 4 can be appropriately designed in order to achieve an optimized acquisition of both optoacoustic images and ultrasonographic images with only one detector unit 4.

In particular, the size and/or the pitch and/or the spatial arrangement of the first transducer elements in the first surface segments 1 is or are selected such that optoacoustic images are obtained having a desired quality, in particular resolution, field of view, sharpness etc. Likewise, the size and/or the pitch and/or the spatial arrangement of the second transducer elements provided on the second surface element 2 is or are selected such that ultrasonographic images of a desired quality, in particular resolution, field of view, sharpness etc., are obtained.

For example, shape, curvature, and/or size of the second surface segment 2 is optimized for the acquisition of pulse-echo ultrasound images. Preferably, the covered field of view can be effectively adjusted by the curvature of the second surface segment 2. In the present example, the second surface segment 2, on which the second transducer elements are provided, has a convex shape by which the effective field of view in the pulse-echo ultrasound mode is expanded. Moreover, the pitch and/or the number of the second transducer elements are designed such that side lobes for a given frequency are minimized and/or the image quality is optimized via spatial compounding. For instance, the second transducer elements form an ultrasound phased array consisting of 128 elements with a central frequency of 6 MHz and a pitch size in the range of approximately 0.4 mm.

For example, the first surface segment 1, on which the first transducer elements are provided, is designed to cover the entire or at least a major part of the circumference of the imaged object 10. Preferably, the first transducer elements, which are arranged on the first surface segments 1 of the detector unit 4, may have a pitch size, in particular a width, which is larger than the size of the second transducer elements. Alternatively or additionally, the pitch of the first transducer elements may be larger than the pitch of the second transducer elements. In this way, good detection sensitivity in the optoacoustic mode is achieved. For example, for the same central frequency the width of the first transducer elements can be approximately in the range of 1 mm.

For example, in a two-dimensional, i.e. cross-sectional, imaging configuration, both the first transducer elements and the second transducer elements of the detector unit 4 may be focused cylindrically in order to deliver cross-sectional images in both ultrasound and optoacoustic modes.

In FIG. 1, the detector unit 4 is represented in a cross-sectional view. Accordingly, the first surface segments 1 and the second surface segment 2 may be constituted by strip-like curved arrays of first and second transducer elements, respectively. For example, each of the first surface segments of the detector unit 4 may be formed by a one-dimensional array of first transducer elements and/or the second surface segment 2 of the detector unit 4 may be formed by a one-dimensional array of second transducer elements.

Alternatively or additionally, the first and/or second surface segments 1 and 2, respectively, may be constituted by curved two-dimensional arrays of first and/or second transducer elements. For example, the first surface segments 1 may have a shape that corresponds to the shape of segments of a cylindrical or spherical surface. Likewise, the second surface segment 2 may have a shape that corresponds to the shape of a cylindrical or spherical surface.

In the given example, the second surface segment 2 abuts to the first surface segments 1, whereby a continuous detector surface, on which first and second transducer elements are arranged, is obtained.

In the following, further examples of devices for hybrid optoacoustic and ultrasonic imaging with various designs of the detector unit 4 and/or the irradiation unit 3 will be described in detail. For sake of simplification, the control unit 20 and the display unit 21 are not shown. However, the above elucidations regarding image formation and display apply accordingly. Moreover, the above elucidations relating to any other aspect of the first example given in FIG. 1 apply, unless otherwise stated, accordingly to the examples given below.

Figure 2:
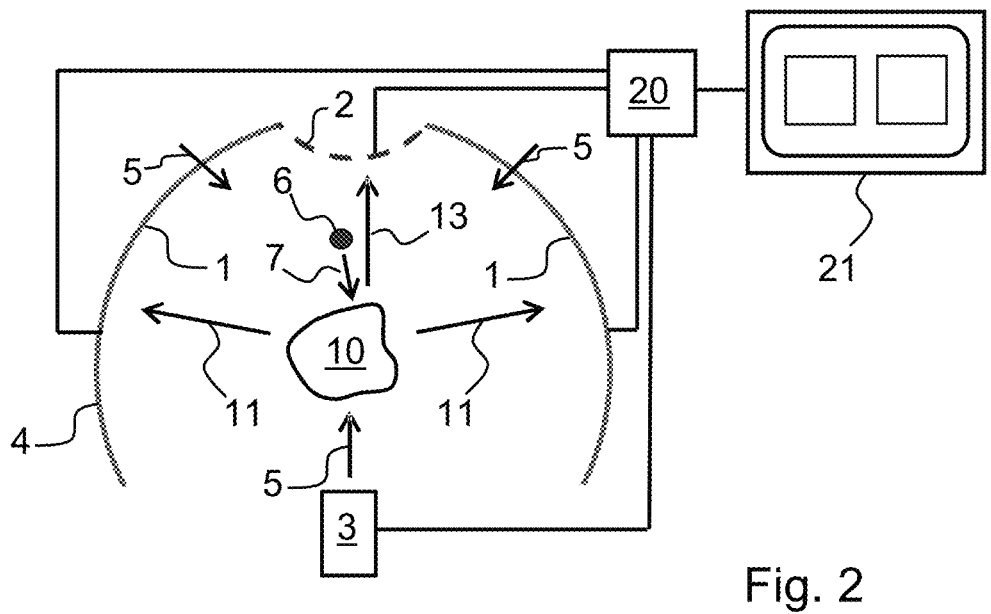
FIG. 2 a schematic representation of a second example of a device for hybrid optoacoustic and ultrasonographic imaging including a cross-sectional view of a detector unit.

FIG. 2 shows a second example of a device for hybrid optoacoustic and ultrasonic imaging, wherein the first surface segments 1 of the detector unit 4 comprise a plurality of first transducer elements which are configured to detect the ultrasound waves 11 that are generated in the object 10 upon irradiation with the electromagnetic radiation 5. An additional absorption element 6 is placed between the imaged object 10 and the surface segments 1 and/or 2 of the detector unit 4. Ultrasound waves 7 are generated in response to an absorption of electromagnetic waves 5 in said absorption element 6 and emitted towards the imaged object 10. The second surface segment 2 of the detector unit 4 comprises a plurality of second transducer elements which are configured and/or controlled to only detect ultrasound waves 13 which are reflected and/or transmitted by the object 10. As a result, the detector unit 4 is configured to detect both optoacoustically generated ultrasound waves 11, which can be further processed in order to obtain optoacoustic images of the object 10, and ultrasonic waves 13, which are further processed in order to obtain ultrasonographic images of the object 10.

Preferably, the additional absorption element 6 has characteristic dimensions that allow for generation of high-frequency ultrasound signals via absorption of short-pulsed electromagnetic radiation. In this way, pulse-echo ultrasound images of the object can be formed with superior spatial resolution. An example of such an element is an absorbing microsphere with diameter of 100 μm that emits broadband spherical ultrasound waves with peak frequency at ~7.5 MHz upon absorption of laser pulse with duration below 10 nsec. Another example is an absorbing foil, which emits broadband planar ultrasound waves upon absorption of short laser pulses.

Figure 3:
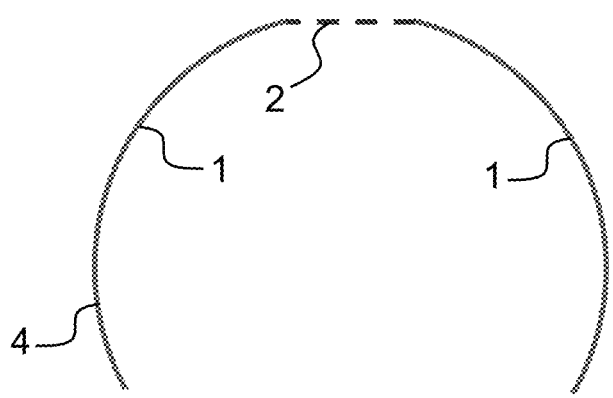
FIG. 3 a cross-sectional view of a detector unit of a third example of a device for hybrid optoacoustic and ultrasonographic imaging.
Figure 4:
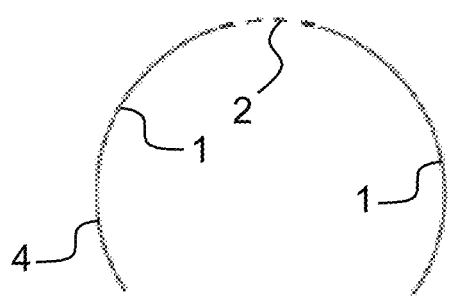
FIG. 4 a cross-sectional view of a detector unit of a fourth example of a device for hybrid optoacoustic and ultrasonographic imaging.

FIG. 3 shows a cross-sectional view of a detector unit 4 of a third example of a device for hybrid optoacoustic and ultrasonic imaging, wherein the first surface segments 1, on which the first transducer elements are provided, are curved, whereas the second surface element 2, on which the second transducer elements are provided, is planar. In the fourth example shown in FIG. 4 both the first surface segments 1 and the second surface segment 2 have a concave shape.

As already explained in connection with the first example given in FIG. 1, the arrays of transducer elements provided on the first surface segments 1 and the second surface segment 2 may comprise one- or two-dimensional arrays of transducer elements, wherein the first and/or second surface segments 1 or 2, respectively, have a strip-like shape or a cylindrical, spherical or bowl-like shape.

Figure 5:
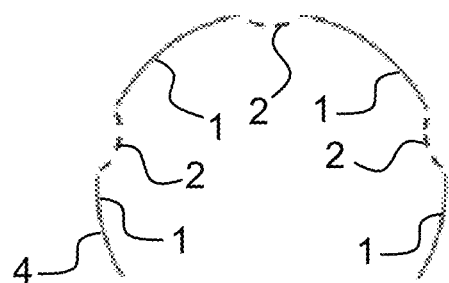
FIG. 5 a cross-sectional view of a detector unit of a fifth example of a device for hybrid optoacoustic and ultrasonographic imaging.

FIG. 5 shows a cross-sectional view of a detector unit 4 of a fifth example of the device, wherein in total four first surface segments 1 and three second surface segments 2 are provided. Thus, second transducer elements are not only provided to face one side of the object 10 (see FIGS. 1 to 4), but rather to face in total three different sides of the object, whereby ultrasonographic image acquisition is further improved without considerably affecting the image quality of the optoacoustic images obtained from the signals generated by the first transducer elements provided on the first surface segments 1.

Figure 6:
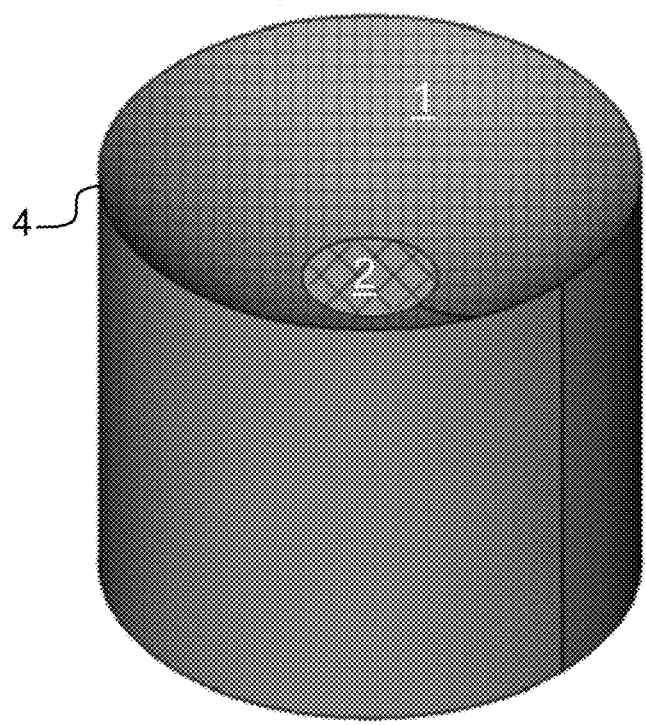
FIG. 6 a perspective view of a detector unit of a sixth example of a device for hybrid optoacoustic and ultrasonographic imaging.

FIG. 6 shows perspective view of a detector unit 4 of a sixth example of a device which is particularly suited for volumetric, i.e. three-dimensional, hybrid optoacoustic and ultrasonographic imaging. The detector unit 4 comprises a two-dimensional concave first surface segment 1 on which first transducer elements are provided. The first surface segment 1 is part of a surface of a recess that is provided in the detector unit 4. Preferably, at the bottom of the surface of the recess a planar second surface segment 2, on which second transducer elements are arranged, is provided. Preferably, the object to be imaged is placed and/or held in a position within the recess of the detector unit 4. Alternatively, the object can also be placed outside the recess.

Figure 7:
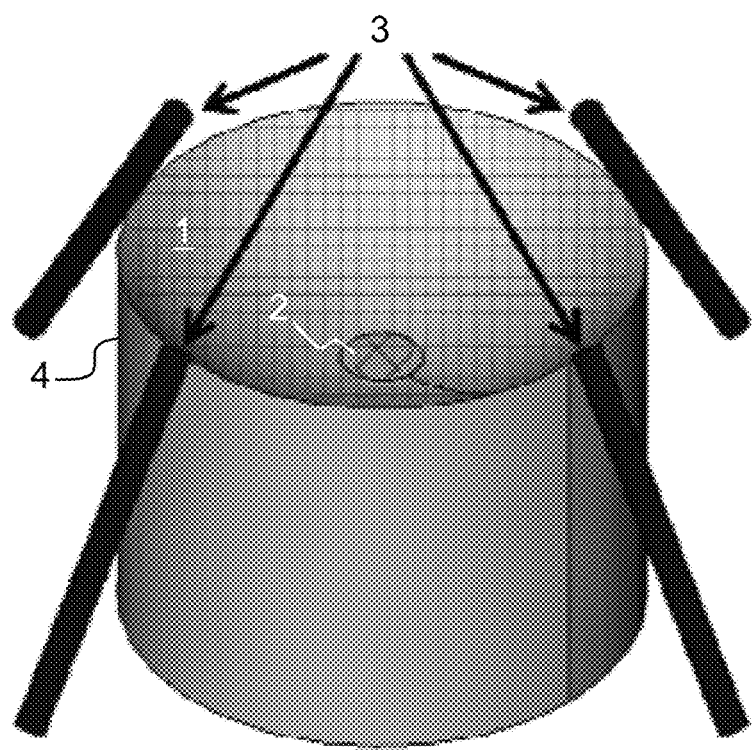
FIG. 7 a perspective view of a detector unit and an illumination unit of a seventh example of a device for hybrid optoacoustic and ultrasonographic imaging.

In order to irradiate the object with electromagnetic radiation, in particular light, an irradiation unit 3 can be provided outside the detection unit 4. This is exemplarily shown in FIG. 7, wherein the irradiation unit 3 comprises four light-guiding elements by which light is guided towards the object (not shown). The light-guiding elements can be, for example, fiber bundles.

Figure 8:
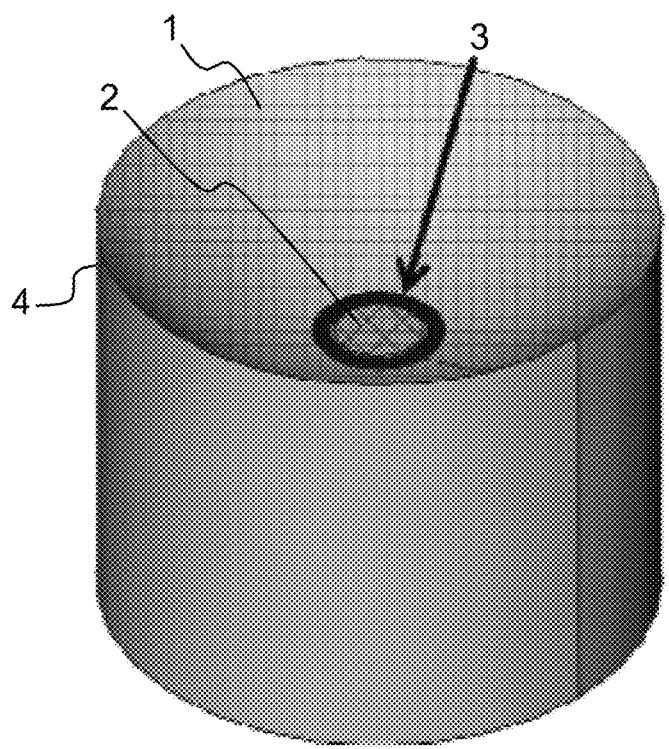
FIG. 8 a perspective view of a detector unit and an illumination unit of a eighth example of a device for hybrid optoacoustic and ultrasonographic imaging.

In the example of the detection unit 4 shown in FIG. 8, the irradiation unit 3 is provided in the region of a surface segment of the recess surface of the detection unit 4 which is between the first surface segment 1 and the second surface segment 2. For example, a fiber bundle having a ring-shaped cross-section is provided in an aperture between the first surface segment 1 and the second surface segment 2.

Figure 9:
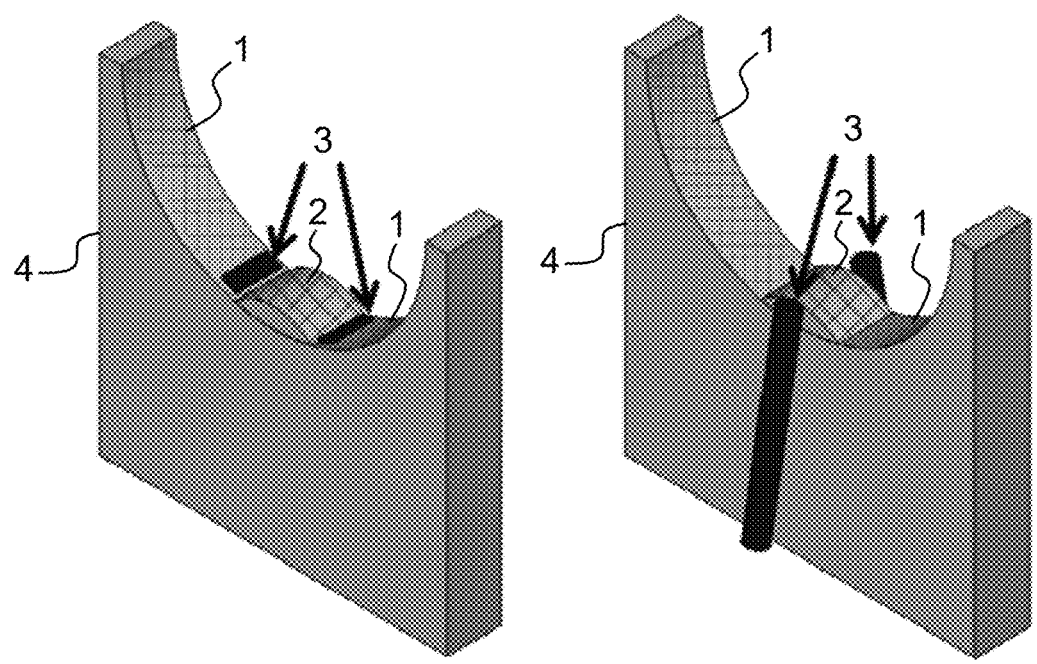
FIG. 9 a perspective view of a detector unit and an illumination unit of a an ninth (left) and tenth (right) example of a device for hybrid optoacoustic and ultrasonographic imaging.

Likewise, as illustrated in the examples given in FIG. 9 the irradiation unit 3 may be provided in a transitional region between strip-like concave first surface segments 1 and a strip-like convex surface segment 2 (left part of FIG. 9) or outside the strip-like surface segments 1 and 2 (right part of FIG. 9). In the latter case, light guiding elements of the irradiation unit 3 are preferably placed near to the bottom and/or the center of the concave surface of the detector unit 4.

Figure 10:
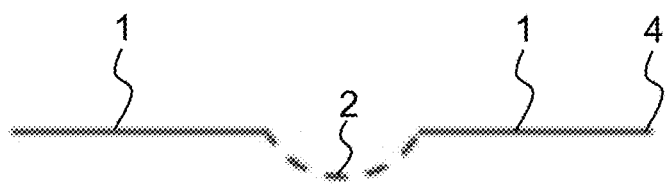
FIG. 10 a cross-sectional view of a detector unit of a eleventh example of a device for hybrid optoacoustic and ultrasonographic imaging.

In FIG. 10 a cross-sectional view of another example of a detector unit 4 is shown, wherein the first surface segments 1, on which first transducer elements are provided, are planar, whereas a second surface segment 2, on which the second transducer elements are provided, has a concave or convex curvature.

Figure 11:
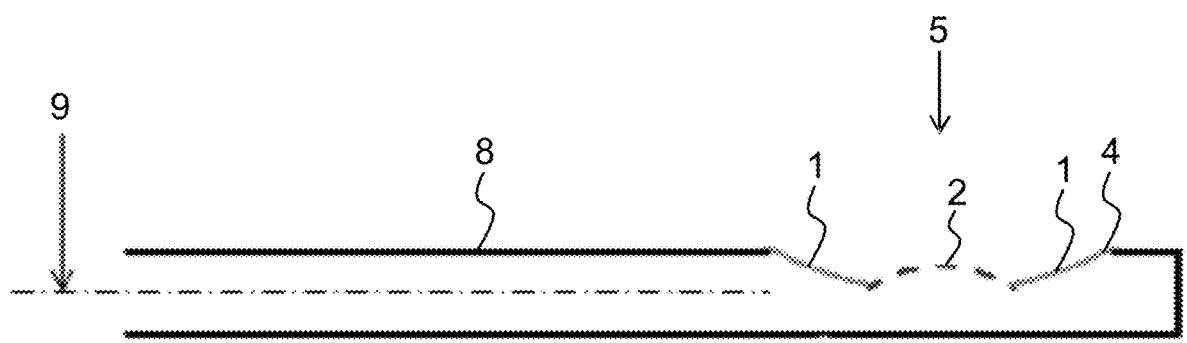
FIG. 11 a cross-sectional view of a probe for endoscopic or intravascular imaging comprising a detector unit of an twelfth example of a device for hybrid optoacoustic and ultrasonographic imaging.

FIG. 11 shows a cross-sectional view of another example of a device which is particularly suited for endoscopic or intravascular imaging by means of optoacoustic and pulse-echo ultrasound imaging. In the present example, a probe 8 that is to be inserted into the object to be investigated, is provided with a detector unit 4 that has a similar design as the one shown in the examples of FIG. 1 or FIG. 9, wherein a surface of a recess provided at a distal end of the probe 8 is constituted by two concave first surface segments 1 and a convex second surface segment 2 in between. Electromagnetic radiation 5 is irradiated by an irradiation unit (not shown) from outside of the probe 8. Alternatively or additionally, the irradiation unit can be located, for example in an aperture between the first surface segments 1 and the second surface segments 2, as exemplarily shown in FIG. 8 and FIG. 9 (left part). In the present example, the first and/or second transducer elements that are provided on the first surface segments 1 or second surface segments 2, respectively, are preferably cylindrically focused in the imaging plane, whereby cross-sectional images of a plane that is perpendicular to probe axis 9 are readily acquired. Preferably, the probe 8 is configured to be rotated around its axis 9 to provide images from different planes. Alternatively, the first and/or second transducer elements may have an unfocused, i.e. a planar, shape, wherein complete data sets for three-dimensional image reconstruction can be obtained after a full 360°-rotation of the probe 8.

According to a preferred aspect of the invention, the resolution, in particular the spatial and/or temporal resolution, of the optoacoustic and ultrasonographic images to be obtained and/or the field of view of the first surface section 1 and/or the second surface section 2 of the detector unit 4 are matched. This can be done by varying the different characteristics of the first and second transducer elements, e.g. the central frequency of each segment, its curvature and orientation in space, size, pitch and focusing characteristics of the individual elements, duration of the emitted ultrasound or light pulses, size of any additional absorbing elements placed in between the imaged object and the surface sections 1 and/or 2. In this context, the term 'matched' implies a design in which one or more of the above mentioned image characteristics (spatial and/or temporal resolution and/or field of view) are equal for both optoacoustic and ultrasound images or differ by any given percentage value, e.g. up to 10%. Alternatively or additionally, the resolution of the optoacoustic and ultrasonographic images and/or the field of view of the first surface section 1 and/or the second surface section 2 of the detector unit 4 are optimized for a given application. For instance, the field of view of the ultrasound image may cover an entire imaged object while the field of view of optoacoustic images only covers a small portion of the imaged object. Likewise, a temporal resolution of the images may differ substantially if suitable for the particular application. For instance, if fast signal dynamics is only expected in the optoacoustic images, the ultrasound images are only acquired for every e.g. 10 or 100 optoacoustic image thus saving on the acquired and processed data volumes. Similar considerations can be applied to the spatial resolution of the images. For instance, if the ultrasound images are only used for very coarse anatomical guidance while the optoacoustic images are expected to provide very accurate physiological or molecular information with high spatial resolution, the spatial resolution of the ultrasound images can be designed to be substantially lower than the corresponding resolution of the optoacoustic images. As an alternative example, the surface segment 2 can be designed to provide high spatial resolution in the ultrasound mode while surface segment 1 is designed such that its elements have a large size in order to increase their sensitivity in detecting weak optoacoustic responses. In this case, the optoacoustic images will have very coarse spatial resolution, which will be partially compensated by providing ultrasound images with much better spatial resolution. The way of designing the first and second surface sections with the desired parameters will be elucidated in detail in the following.

Ultrasonographic Images

Figure 12:
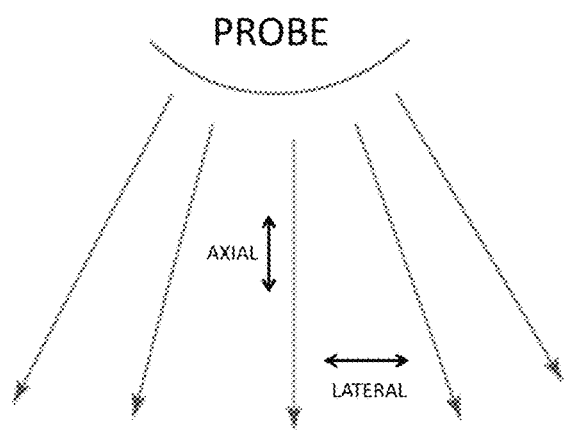
FIG. 12 a schematic representation of ultrasonic waves emerging from a probe.

The axial and lateral resolution of ultrasound images obtained with the ultrasound array formed by the second transducer elements of the second surface segment 2 is determined as follows (see FIG. 12):

The axial resolution (AR) is determined by the spatial pulse length (SPL) as $AR=SPL/2=N_{cycles}*\lambda/2$, where $\lambda=c/f$ is the acoustic wavelength for the given central frequency f of the emitted ultrasound pulse (c is the speed of sound) and $N_{cycles}$ denotes the effective number of cycles in the emitted ultrasound pulse.

The lateral resolution (LR) is determined by the focusing capacity of the ultrasound beam produced by the array via $LR=\lambda F/D$, where F is the focal distance and D is the size (aperture) of the array. The lateral resolution is optimal at the focus and degrades as the object is moved away from the focus. Preferably, in order to maintain the lateral resolution in a larger field of view, dynamic beamforming is used to focus at different depths, which can be done by e.g. shifting the phase of the pulses transmitted and/or received by the individual array elements.

The field of view of the ultrasound images obtained with the ultrasound array formed by the second transducer elements of the second surface segment 2 is adaptable depending on the application and the conditions of the achievable temporal resolution of the images (see FIG. 12):

The maximum axial size of the field of view is determined by the pulse repetition rate of the ultrasound pulses so that two consecutive pulse-echo signals do not overlap. On the other hand, frequency-dependent acoustic attenuation limits the achievable depth and then the axial size of the field of view.

The lateral field of view depends on the number of lines used to form the B-mode image and can also be adapted to the particular application.

Figure 13:
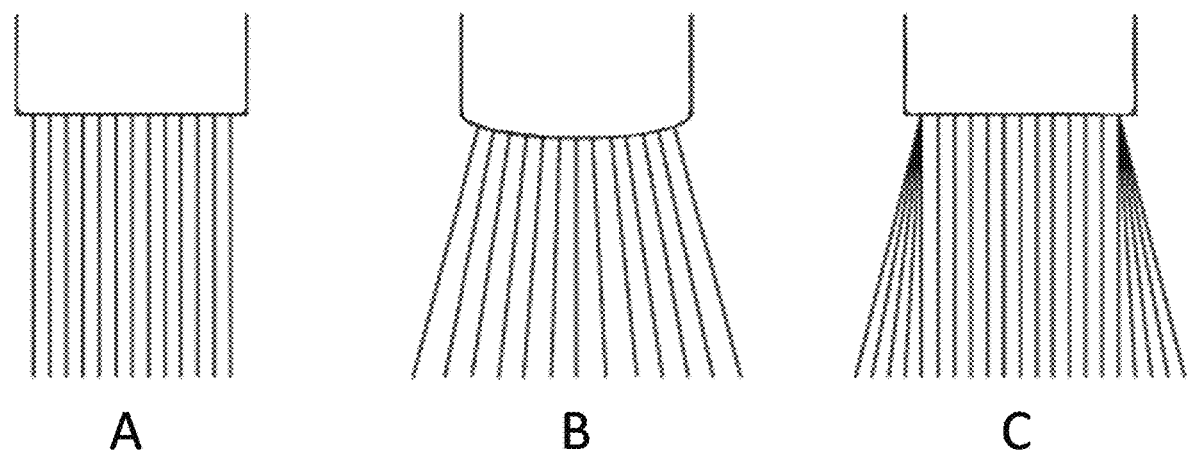
FIG. 13 a schematic representation of three examples of arrays of second transducer elements having a different field of view.

FIG. 13 illustrates examples of different approaches to acquire the ultrasound beams that represent the lines in the B-mode image. Generally, the ultrasound beams are perpendicular to the surface of the line of the second transducer elements, although by means of beamforming it is also possible to direct the beam when using a line array, as exemplarily shown in the trapezoidal field of view in FIG. 13(c).

Optoacoustic Images

In the case of tomographic optoacoustic imaging with full angular coverage, the resolution (R) of optoacoustic images obtained with the array formed by the first transducer elements of the first surface segment 1 is determined by the bandwidth ($\Delta f$) of the ultrasound transducer employed and can be approximated as $R=c/\Delta f$, where c is the speed of sound in the imaged medium The field of view (FOV) of the optoacoustic images obtained with the ultrasound array formed by the first transducer elements of the first surface segment 1 is determined by diffraction from the size of the individual first transducer elements of the optoacoustic transducer array. In the case that the optoacoustic signals are broadband signals, the field of view is determined by the frequency content of the signals emitted by different absorbers. For example, small absorbers emitting high frequencies are visualized in a small FOV, whereas large absorbers emitting low acoustic frequencies can be seen in a big FOV. Considering a given central frequency $f_c$ of the first transducer elements, the expected FOV is approximately $FOV=2.44cR/df_c$, where R is the radius of the array, i.e. the radius of the first surface segment(s) 1, and d is the characteristic size (or pitch) of the first transducer elements. For instance, given a cylindrically focused array, as shown in FIG. 1, with its first transducer elements cylindrically focused in a certain imaging plane, having the following characteristics—radius of curvature of 4 cm; element size of 1 mm; central frequency of 5 MHz— the effective FOV in the imaged plane will have a size of approximately 2.9 cm around the center of the curvature.

The invention claimed is:

1. A device for hybrid optoacoustic and ultrasonographic imaging of an object, the device comprising:
    an irradiation unit comprising a laser or light-guiding elements irradiating the imaged object with electromagnetic radiation,
    first transducer elements detecting ultrasound waves generated in the object upon irradiating the object with the electromagnetic radiation,
    second transducer elements emitting ultrasound waves towards the object and detecting ultrasound waves reflected and/or transmitted by the object, and
    a surface comprising at least one first surface segment, on which the first transducer elements are arranged, and at least one second surface segment, on which the second transducer elements are arranged,
    wherein the at least one first surface segment, on which the first transducer elements detecting ultrasound waves generated in the object upon irradiating the object with the electromagnetic radiation are arranged, has a curved shape, wherein said first transducer elements, which detect ultrasound waves generated in the object upon irradiating the object with the electromagnetic radiation, have a first size and a first pitch and said second transducer elements, which detect ultrasound waves reflected and/or transmitted by the object, have a second size and a second pitch, wherein the first pitch is different from the second pitch and/or the first size is different from the second size, wherein ultrasound waves generated, due to the optoacoustic effect, in response to an absorption of the electromagnetic radiation at the at least one first surface segment and/or at the at least one second surface segment are emitted towards the imaged object and, after reflection and/or transmission by the imaged object, are detected by the second transducer elements and wherein at least one absorbing element is provided between the imaged object and the first surface segment and/or the second surface segment, the absorbing element generating ultrasound waves in response to an absorption of the electromagnetic radiation.

2. The device according to claim 1, the absorbing element being configured to generate high-frequency ultrasound waves in response to an absorption of pulsed electromagnetic radiation.

3. The device according to claim 1, wherein the absorbing element comprises at least one electromagnetic radiation absorbing microsphere emitting ultrasound waves in response to an absorption of electromagnetic radiation, wherein the at least one electromagnetic radiation absorbing microsphere has a diameter in the range between 50 µm and 500 µm and/or emits ultrasound waves exhibiting a peak frequency in the range between 4 and 10 MHz in response to an absorption of a laser pulse having a duration below 100 ns.

4. The device according to claim 1, the absorbing element comprising at least one electromagnetic radiation absorbing foil configured to emit broadband planar ultrasound waves in response to an absorption of short laser pulses.

5. The device according to claim 1, wherein
the at least one first surface segment has a concave shape; and/or
the at least one second surface segment has a convex shape; or
the at least one second surface segment has a planar shape.

6. The device according to claim 1, wherein the first pitch is larger than the second pitch and/or the first size is larger than the second size.

7. The device according to claim 1, the first transducer elements being adjacent to each other and/or the second transducer elements being adjacent to each other.

8. The device according to claim 1, the surface being a continuous surface which is formed by the at least one first surface segment and the at least one second surface segment.

9. The device according to claim 1, the device comprising a control unit configured
to reconstruct a first image based on the detected ultrasound waves generated in the object upon irradiating the object with the electromagnetic radiation, the first image exhibiting a first resolution and a first field of view, and
to reconstruct a second image based on the detected ultrasound waves reflected and/or transmitted by the object, the second image exhibiting a second resolution and a second field of view.

10. The device according to claim 9, wherein at least one of the first resolution, the first field of view, the second resolution and the second field of view is or are optimized and/or matched.

11. The device according to claim 9, the control unit being configured
to reconstruct the first image using second information, which is contained in at least one reconstructed second image, and/or
to reconstruct the second image using first information, which is contained in at least one reconstructed first image.

12. The device according to claim 11, wherein
the second information relates to locations of acoustic scatterers and/or heterogeneities in the object and is contained in at least one second image, which has been reconstructed based on the detected ultrasound waves reflected by the object, and/or
the second information relates to the speed of sound and/or acoustic attenuation in the object and is contained in at least one second image, which has been reconstructed based on the detected ultrasound waves transmitted by the object.

13. A method for hybrid optoacoustic and ultrasonographic imaging of an object, the method comprising the following steps:
irradiating the object with electromagnetic radiation,
detecting ultrasound waves, which are generated in the object upon irradiating the object with the electromagnetic radiation, by first transducer elements, which are arranged on at least one first surface segment of a surface,
emitting ultrasound waves towards the object and detecting the ultrasound waves, which are reflected and/or transmitted by the object, by second transducer elements, which are arranged on at least one second surface segment of the surface,
wherein the at least one first surface segment, on which the first transducer elements detecting ultrasound waves generated in the object upon irradiating the object with the electromagnetic radiation are arranged, has a curved shape, said first transducer elements, which detect ultrasound waves generated in the object upon irradiating the object with the electromagnetic radiation, have a first size and a first pitch and said second transducer elements, which detect ultrasound waves reflected and/or transmitted by the object, have a second size and a second pitch, wherein the first pitch is different from the second pitch and/or the first size is different form the second size,
wherein ultrasound waves generated, due to the optoacoustic effect, in response to an absorption of the electromagnetic radiation at the at least one first surface segment and/or at the at least one second surface segment are emitted towards the imaged object and, after reflection and/or transmission by the imaged object, detected by the second transducer elements, and
providing at least one absorbing element between the imaged object and the first surface segment and/or the second surface segment, the absorbing element generating ultrasound waves in response to an absorption of the electromagnetic radiation.

* * * * *